(12) United States Patent
Crosson et al.

(10) Patent No.: US 8,181,544 B2
(45) Date of Patent: May 22, 2012

(54) LIQUID SAMPLE EVAPORATOR FOR VAPOR ANALYSIS

(75) Inventors: Eric Crosson, Mountain View, CA (US); Bruce A. Richman, Sunnyvale, CA (US); Bruce H. Vaughn, Boulder, CO (US); James W. C. White, Boulder, CO (US)

(73) Assignees: Picarro, Inc., Santa Clara, CA (US); The Regents of the University of Colorado, Denver, CO (US)

( * ) Notice: Subject to any disclaimer, the term of this patent is extended or adjusted under 35 U.S.C. 154(b) by 690 days.

(21) Appl. No.: 12/313,375

(22) Filed: Nov. 18, 2008

(65) Prior Publication Data

US 2010/0122564 A1     May 20, 2010

(51) Int. Cl.
*G01N 1/38*    (2006.01)
*G01N 1/34*    (2006.01)
*G01N 1/44*    (2006.01)
*G01N 33/18*   (2006.01)
*G01N 30/12*   (2006.01)

(52) U.S. Cl. ............ 73/864.85; 73/1.03; 73/23.21; 73/64.56; 73/863.11; 73/864.86; 73/864.87; 702/100

(58) Field of Classification Search .. 73/864.83–864.87, 73/1.03, 23.21–23.22, 64.56, 863.11, 1.06, 73/23.36, 23.41–23.42, 61.55–61.57, 61.59, 73/863, 864.81; 702/100, 198, FOR. 167
See application file for complete search history.

(56) References Cited

U.S. PATENT DOCUMENTS

| | | | | |
|---|---|---|---|---|
| 3,118,300 A | * | 1/1964 | Jenkins | 73/864.84 |
| 3,174,326 A | * | 3/1965 | Carle et al. | 73/23.41 X |
| 3,247,704 A | * | 4/1966 | Konig | 73/23.41 |
| 3,753,654 A | * | 8/1973 | Eggertsen | 436/154 |
| 3,798,973 A | * | 3/1974 | Estey | 73/864.81 X |
| 3,889,538 A | * | 6/1975 | Fingerle | 73/863.11 |
| 4,057,393 A | * | 11/1977 | Budzak et al. | 436/141 |
| 4,135,881 A | * | 1/1979 | Bakx et al. | 436/139 |
| 4,414,857 A | * | 11/1983 | Brazhnikov et al. | 73/863.11 |
| 4,704,141 A | * | 11/1987 | Krebber | 73/23.41 X |
| 4,708,013 A | * | 11/1987 | Landis | 73/23.41 X |
| 4,766,760 A | * | 8/1988 | Poshemansky et al. | 73/23.42 X |
| 5,174,149 A | * | 12/1992 | Grob et al. | 73/23.41 |
| 5,917,184 A | | 6/1999 | Carson et al. | |
| 6,166,379 A | | 12/2000 | Montaser et al. | |
| 6,707,035 B2 | | 3/2004 | Hughey et al. | |
| 7,317,186 B2 | | 1/2008 | Montaser et al. | |

FOREIGN PATENT DOCUMENTS

| | | | |
|---|---|---|---|
| DE | 3511687 A1 | * 10/1985 | |
| DE | 19836913 A1 | * 2/2000 | |
| EP | 461438 A2 | * 12/1991 | 73/863.11 |

(Continued)

*Primary Examiner* — Thomas P Noland
(74) *Attorney, Agent, or Firm* — Lumen Patent Firm

(57) ABSTRACT

Preparation methods for introducing liquid samples to gas analysis instruments include 1) complete evaporation of a liquid sample in a sample chamber, and 2) allowing the sample vapor in the sample chamber to equilibrate for a predetermined time. An inert carrier gas (e.g., dry nitrogen or zero air) is also admitted to the sample chamber. After equilibration, the sample vapor is admitted as a conditioned sample to an analysis instrument. Preferably, the predetermined equilibration time is sufficiently long that the sample vapor in the sample chamber becomes substantially homogeneous with respect to both concentration and isotopic ratio. Vapor derived from a liquid calibration standard in this manner can be employed as an accurate gas-phase calibration reference.

26 Claims, 6 Drawing Sheets

FOREIGN PATENT DOCUMENTS

| | | | | |
|---|---|---|---|---|
| JP | 52052689 A | * | 4/1977 | .......... 250/380 |
| JP | 01021352 A | * | 1/1989 | .......... 422/80 |
| JP | 06117972 A | * | 4/1994 | .......... 73/29.01 |
| SU | 1343346 A | * | 10/1987 | |

* cited by examiner

LIQUID SAMPLE EVAPORATOR FOR VAPOR ANALYSIS

GOVERNMENT SPONSORSHIP

This invention was made with US government support under contract number 2 R44 RR021297 awarded by the National Institutes of Health. The government has certain rights in this invention.

FIELD OF THE INVENTION

This invention relates to preparation of liquid samples for vapor phase analysis.

BACKGROUND

Concentration and/or isotopic ratio analysis systems are most often configured to accept gaseous samples. Such analysis systems can be based on various physical principles, such as mass spectrometry, cavity ring-down spectroscopy, cavity enhanced absorption spectroscopy, etc. Independent of the analysis technology employed, special measures are needed to accommodate liquid samples in such analysis.

Known approaches for providing analysis of liquid samples include electrospray of a liquid sample into a spray chamber connected to an analysis instrument (mass spectrometer), as described in U.S. Pat. No. 5,917,184. Another conventional approach is the use of nebulizers, as in U.S. Pat. Nos. 6,166,379 and 7,317,186.

SUMMARY

However, it has been found that such conventional approaches for handling liquid samples may not provide adequate performance for demanding applications, such as isotopic ratio measurements of water. Isotopic ratio measurements of oxygen and hydrogen in liquid and vapor water have important applications in environmental monitoring, biomedical diagnostics, and other industrial, medical, and research fields of interest. Since water isotopic calibration standards exist only in liquid form (e.g., Vienna Standard Mean Ocean Water (VSMOW) as provided by the International Atomic Energy Agency (IAEA)), an isotopic water vapor analyzer can be calibrated only if the liquid standards are converted to vapor. This must be done with careful control so that the isotopic content of the vapor is identical to that of the liquid. The combination of an isotopic water vapor analyzer with an apparatus to convert liquid water to vapor is crucial for calibrating any water vapor isotopic measurements, and because calibrations are an essential element of producing credible isotopic analyses of water or water vapor, this represents an important step forward in alternative water isotope analysis.

If a volume of liquid water is evaporated over a period of time, the isotopic content of the vapor will vary as a function of time. If evaporation is incomplete (some liquid remains at the end of the time), then the isotopic content of the entire volume of vapor will likely be different from both the original and remaining liquid, e.g. because of temperature-dependent fractionation during evaporation. In theory, the simplest way to guarantee that the isotopic content of the vapor is identical to that of the original liquid sample is to evaporate all of the liquid and to collect and analyze the entire resulting vapor. If all of the water vapor is analyzed, the measurement can determine the isotopic content of the liquid which generated the vapor. However, even this does not automatically guarantee that the measurement of the isotopic content of the vapor matches the isotopic content of the liquid. The results of isotopic measurement of the vapor depend on the method used to evaporate the sample, to analyze the vapor, and the interaction of these two methods.

To address this technical problem, embodiments of the invention rely on sample preparation methods including 1) complete evaporation of a liquid sample in a sample chamber (also referred to an evaporator), and 2) allowing the sample vapor in the sample chamber to equilibrate for a predetermined time. An inert carrier gas (e.g., dry nitrogen or zero air) is also admitted to the sample chamber. After equilibration, the sample vapor is admitted as a conditioned sample to an analysis instrument. Preferably, the predetermined equilibration time is sufficiently long that the sample vapor in the sample chamber becomes substantially homogeneous with respect to both concentration and isotopic ratio.

This sample vapor homogeneity is a key feature of embodiments of the invention, and provides numerous advantages. More specifically, the concentration and isotopic ratios of the conditioned sample do not significantly change as the conditioned sample flows into the analysis instrument. As a result, a single measurement of the conditioned sample provides a rapid measurement that is properly representative of the original liquid sample. Another consequence of this flow uniformity is that multiple measurements of the conditioned sample can be made and averaged to improve measurement accuracy.

This desirable behavior is in sharp contrast to conventional situations where the flow of an evaporated liquid sample into the analyzer is not made uniform. In such cases: a) the entire volume of vapor must be analyzed; b) the concentration, isotopic ratios and the flow rate must each be measured (and/or accurately controlled) as a function of time during the period of gas flow; and c) the isotopic ratio of the liquid must be determined by integrating the measured gas isotopic ratio weighted by the concentration and flow rate. Steps a-c above lead to complications and inaccuracy in the isotopic ratio determination of the liquid. Additional measurements and/or controls are required (e.g., flow rate), and additional complexity and sources of error are introduced. Embodiments of the invention provide the highly significant advantage of making all of steps a-c above unnecessary.

DETAILED DESCRIPTION

According to embodiments of the invention, liquid samples are prepared for analysis by a method that includes:

a) admitting a first liquid sample to a sample chamber;

b) completely evaporating the first liquid sample in the sample chamber to provide sample vapor;

c) admitting a carrier gas to the sample chamber (the carrier gas can be admitted before the liquid, after the liquid, or some before and some after the liquid);

d) allowing the sample vapor and carrier gas to equilibrate for a predetermined time to provide a conditioned sample in the sample chamber; and e) providing the conditioned sample as an output for analysis.

Preferably this predetermined time is selected so that the conditioned sample has substantially uniform sample vapor concentration and sample vapor isotopic ratio within the sample chamber. The predetermined time is such that the measurement of the conditioned sample vapor during the course of gas flow of the conditioned vapor to analysis for each liquid sample admitted to the sample chamber consistently shows substantially constant concentration and isotopic ratios. Measurements as in FIG. 3 below can be made using various equilibration times to determine the above-described "predetermined time". For example, one could perform flow uniformity measurements for various equilibration times and select the predetermined time to be the smallest of these measured equilibration times that provides a measured flow non-uniformity less than a predetermined threshold (e.g., <1%). For example, given a sample chamber of 150 milliliters volume and 2 microliters of injected liquid water, and with the sample chamber maintained at a temperature of 140 degrees centigrade, the equilibration time is typically in the range of 30 seconds to 3 minutes. Specifically, 90 seconds was used to obtain the data shown in FIG. 3. Further aspects of embodiments of the invention are most conveniently described with reference to apparatus suitable for practicing such embodiments.

Figure 1:
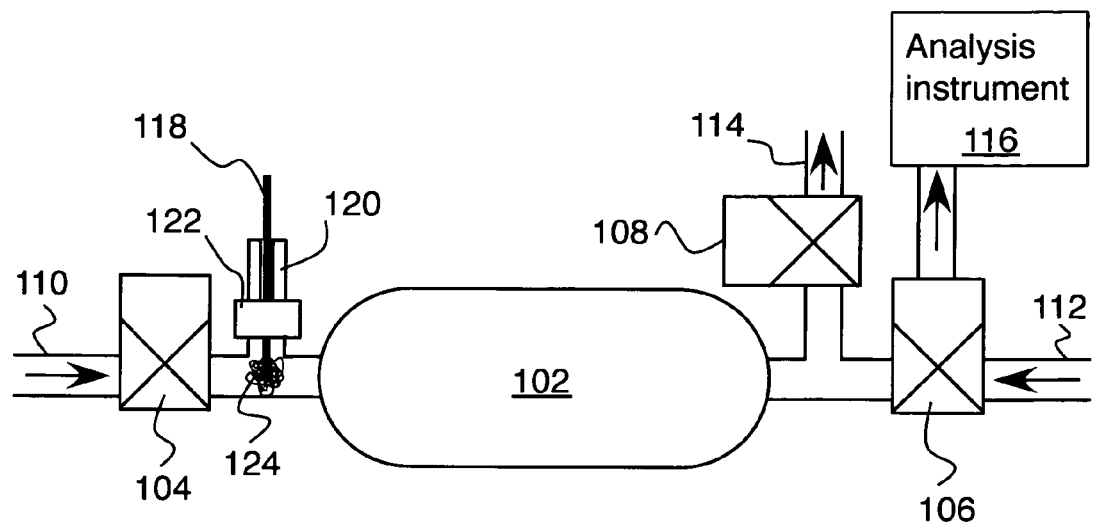
FIG. 1 shows an apparatus suitable for practicing embodiments of the invention.

FIG. 1 shows apparatus suitable for practicing embodiments of the invention. This apparatus includes a chamber 102 connected to an input valve 104, a vacuum valve 108, and a three way valve 106. When input valve 104 is open, carrier gas in input line 110 is admitted to chamber 102. When vacuum valve 108 is open, chamber 102 is connected to vacuum line 114 to purge chamber 102. Three way valve 106 can connect analysis instrument 116 either to chamber 102 or to an alternative input gas line 112. Liquid can be introduced into chamber 102 by a syringe needle 118 which pierces a septum 122 and is mechanically guided by guide 120. Liquid can be dispensed onto a target 124 disposed in the gas input of chamber 102. It is convenient to refer to the system of FIG. 1 as having an analysis instrument 116 and an evaporator that includes everything on FIG. 1 except instrument 116.

Chamber 102 is where the sample vapor mixes with a dry carrier gas, such as nitrogen or zero air. Chamber 102 also serves as a reservoir of sample vapor in carrier gas, from which analysis instrument 116 draws gas to analyze. The chamber and other hardware components exposed to the gas can be made of metal (e.g. steel), glass, plastic, or some other material. It is convenient to use the term "gas-exposed surfaces" to refer to all surfaces of the evaporator which are exposed to vapor from the liquid sample and which are not part of analysis instrument 116. In cases where the liquid sample is a water sample, the gas-exposed surfaces are preferably hydrophobic so as to minimize water adsorption. Sample adsorption is undesirable because it causes fractionation of the isotopic content of the vapor, and also causes contamination (also referred to as "memory") of one liquid sample into the measurement of the following samples. Metals are typically not hydrophobic whereas glass and most plastics (e.g. Teflon™) are hydrophobic. All of the gas-exposed surfaces which are not already hydrophobic preferably have a hydrophobic coating such as Siltek™ or equivalent. Siltek™ is a type of glass-like coating which is hydrophobic. Other possible hydrophobic coatings include but are not limited to Teflon™. In addition all of the hardware having gas-exposed surfaces can preferably withstand temperatures greater than 100° C.

The evaporator of FIG. 1 can be designed to operate in cooperation with and under the control of analysis instrument 116 via control signals. It can alternatively be operated by any other control device using the same control signals. It can also be designed to be used in conjunction with an "autosampler", which is a robotic device which transfers liquid samples from sample containers to other locations (e.g. the evaporator) using a syringe. However, the autosampler is not required for proper operation of the evaporator. Liquid samples can be deposited into the evaporator manually or with any appropriate liquid deposition device, such as a syringe pump, metering pump, or autosampler.

In the example of FIG. 1, liquid water samples are injected through an injection port, which has a vacuum-tight septum 122 that isolates the internal volume of chamber 102 from the ambient air. A syringe 118 containing the liquid sample penetrates the septum, injects the sample, and then withdraws. The water either evaporates directly from the syringe if the chamber is at low pressure (e.g. vacuum), or is deposited onto a target 124 (e.g., glass wool as is commonly used in commercial gas chromatography and mass spectrometry systems). The volume of liquid water injected per sample is preferably between 0.1 and 10 microliters, and more preferably is between 1 and 5 microliters. Appropriate septum materials include rubber and silicone. Commercially available septa such as for gas chromatography and mass spectrometry systems are suitable. Details of liquid sample injection are not critical in practicing embodiments of the invention.

Preferably, the liquid sample handling system provides sample to sample consistency of liquid sample volume. More specifically, on repeated sample injections, each sample will have a corresponding sample volume, which may differ from sample to sample. Preferably, the sample volumes for any given run differ from the average sample volume in that run by less than 10% of the average sample volume.

Figure 2:
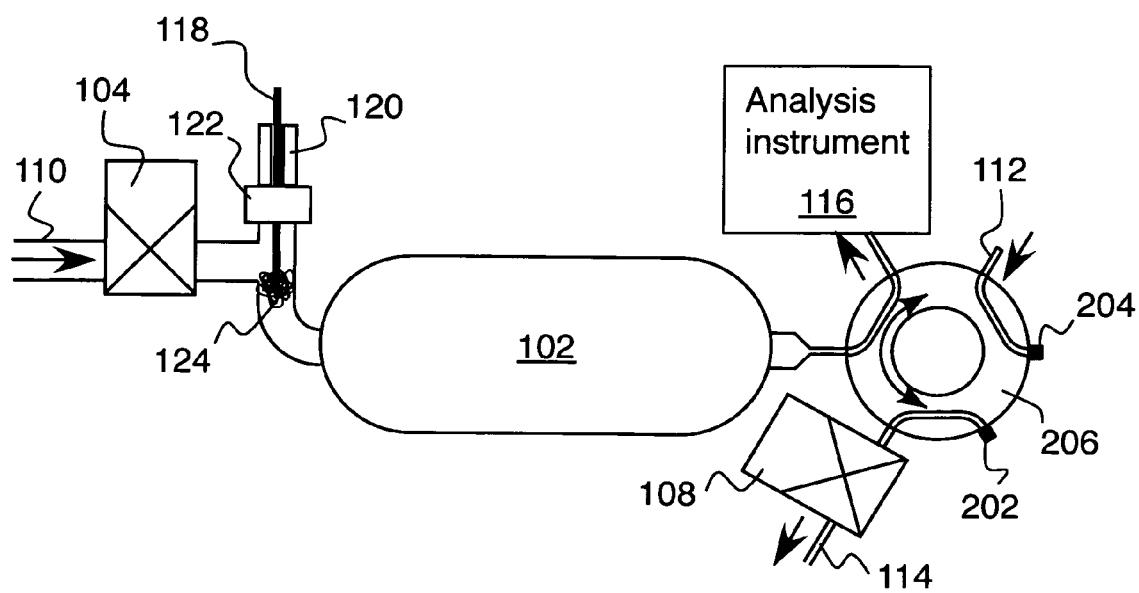
FIG. 2 shows another apparatus suitable for practicing embodiments of the invention.

Input valve 104 allows a dry carrier gas (e.g. a dilution gas) into chamber 102. The vacuum valve 108 connects the chamber with a vacuum (e.g. vacuum line 114 connected to a vacuum pump (not shown)). The 3-way valve 106 selects a gas source to flow to the analysis instrument 116, which is either from chamber 102 or from alternative input gas line 112. Details of the evaporator valve arrangement are not critical in practicing the invention. For example, the locations of the valves around the chamber are not critical. Some configurations have the valves in series (connected to the chamber through another valve instead of directly). The 3-way valve may be replaced by a more complex valve such as one which selects from more than two sources, or a rotary valve which has multiple connections. FIG. 2 shows an example with a rotary valve 206 in place of the 3-way valve 106, and with the vacuum valve 108 in series with rotary valve 206. Plugs 202 and 204 can be provided to prevent useless gas flow. This configuration differs in capability from that shown in FIG. 1 only in that in FIG. 1 the chamber can be simultaneously connected to vacuum line 114 and analyzer 116, whereas in FIG. 2 it cannot be simultaneously connected to both.

The evaporator is preferably maintained at an elevated temperature (e.g. 140° C.) to facilitate evaporation and to reduce adsorption of the sample vapor to gas-exposed surfaces. The chamber, injector and adjacent fittings can be disposed inside a copper tube wrapped in a heater pad. The tube leading from the 3-way valve to the gas analyzer can also be wrapped in a copper case with a heater pad. Materials other than copper which are good heat conductors are also appropriate. A thermal control module can be employed to power the heater pads and to use a thermistor (or other temperature sensor) attached to the chamber to measure the temperature. The evaporator plumbing assembly (in its copper tube) can be wrapped in insulation and mounted inside an aluminum housing. Other embodiments may use different methods of heating and controlling the temperature of the chamber and gas-exposed surfaces, for example heater tape powered by a variable transformer (without active control).

The carrier gas used to dilute and carry the sample vapor can be any gas which does not react with the liquid sample or the hardware, and which does not interfere with operation of analyzer 116. Dry nitrogen and zero air are two preferred choices. Dry air can also be obtained by drawing ambient (humid) air through a drier, such as a tube with desiccant or a cryogenic trap. Perfectly dry gas is ideal for use with liquid water samples, and residual humidity in the carrier gas may degrade the accuracy of the analysis of liquid samples.

Before sample injection, the evaporator is preferably cleaned of the previous liquid sample injection to minimize memory. After injection, the sample (now in vapor form) is prepared by allowing it to equilibrate with the carrier gas. Finally, the water vapor sample is delivered to the gas analyzer. A "cycle" of the valves in the evaporator accomplishes each of these subtasks.

The cycle definition includes a sequence of valve states (open/closed for the gate valves, and evaporator/alternate for the 3-way valve), the duration of each state, and communication with an external injection apparatus between states. The external injection apparatus can be automated, such as with a commercial autosampler, or manually controlled by a human operator.

An exemplary cycle begins immediately after the end of the previous cycle and can be described in terms of the following steps:

First, the cycle switches the 3-way valve to couple the alternate gas source 112 to gas analyzer 116, and evacuates chamber 102 of any remaining gas from the previous sample cycle (e.g., by opening vacuum valve 108). In addition, a signal can be sent to the external injection apparatus to prepare for the next liquid sample injection (e.g., by performing syringe washes and rinses before the actual injection).

Second, the evaporator is flushed with dry carrier gas by opening input valve 104, and evacuated by opening vacuum valve 108, to remove water adsorbed to the surfaces inside the evaporator. This sequence can be repeated more than once to ensure elimination of as much of the previous sample as possible. Three repeats is typical. Each of these sub-cycles will be called a "dry flush." A dry flush can be replaced with a "wet flush," in which the new liquid sample is injected, followed by the carrier gas, and then the evaporator is evacuated. For wet flushes, an instruction can be sent to the external injection apparatus to inject the liquid sample at the appropriate time. A wet flush may be more effective at reducing memory than a dry flush because the removal of adsorbed water molecules without replacement takes energy whereas replacement of adsorbed water molecules with other water molecules takes nominally no energy. Sometimes during a flush sub-cycle, the 3-way valve can be briefly switched to flush the tube leading to gas analyzer 116. The wet flush may alternatively have dry gas allowed into the evaporator before the liquid injection, or both before and after the injection. Also, the input valve and vacuum valve can be open simultaneously for some portion of a flush sub-cycle, to flow gas continuously through the evaporator.

After the flushes, the evaporator is evacuated thoroughly. After evacuation, the evaporator may be fully filled, partially filled, or not filled at all with dry carrier gas. Then, the valves are closed and the controlling device (e.g. the analyzer 116) sends an instruction to the external injection apparatus to inject the liquid sample.

After injection, the external injection apparatus indicates to the controlling device that the injection is complete. The cycle continues by waiting a certain amount of time for the sample water vapor to equilibrate inside the evaporator, then fills the evaporator with the carrier gas (all at once or in multiple stages) if it is not already fully filled, and waits again for the vapor in carrier gas to come to equilibrium inside the evaporator (to ensure that it is well mixed and has uniform properties such as temperature, concentration, and isotopic ratio).

Finally, the 3-way valve 106 changes state to deliver the conditioned sample vapor to gas analyzer 116 for a duration sufficient to effect an accurate analysis. After this delivery is complete, the 3-way valve changes state to deliver the alternate gas to gas analyzer 116. The cycle either repeats immediately to measure another liquid sample, or pauses before repeating so that the alternate gas (e.g. ambient air) is analyzed. The pause can last for a predefined duration, a duration determined dynamically from the analysis, or until it is instructed to perform another liquid sample analysis by an external input (e.g. from a human operator).

Practice of the invention does not depend critically on details of analysis instrument 116, and embodiments of the invention are suitable for introducing vapor samples derived from a liquid into any instrument capable of performing gas analysis. Such instruments include, but are not limited to: mass spectrometers, cavity ring-down spectroscopy instruments, and cavity enhanced absorption spectroscopy instruments. Analysis can include vapor concentration analysis and/or vapor isotopic ratio analysis. Analysis can also include determination of one or more analyte concentrations in the liquid sample.

Figure 3:
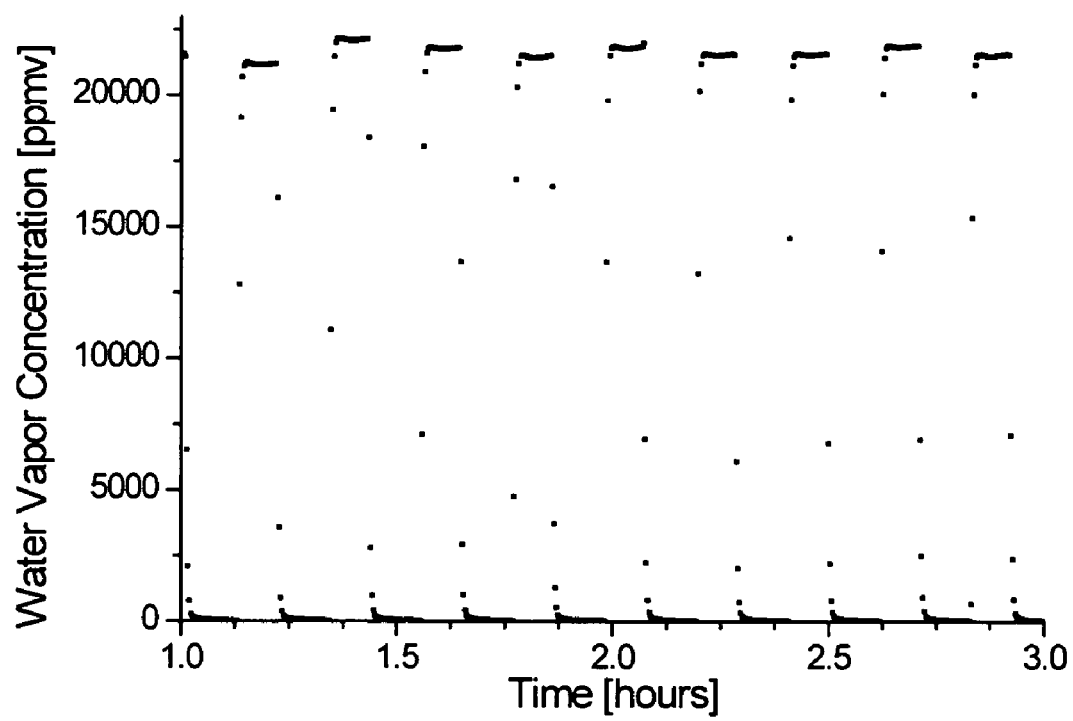
FIG. 3 shows measured water vapor concentration as a function of time from an embodiment of the invention.

FIG. 3 shows an example of water vapor concentration measurements in time provided according to an embodiment of the invention, when the evaporator is accepting liquid samples and cycling without pause. Each pulse of concentration corresponds to the delivery of prepared water vapor in carrier gas from the evaporator to the gas analyzer. The sections of low concentration are when the evaporator is cleaning in preparation for the next liquid sample, and the alternate gas (dry gas in this example) is being provided to the gas analyzer. The evaporator is mostly, but not completely, emptied of the prepared gas by the end of each pulse. One important advantage provided by embodiments of the invention, as described above, is that the water vapor concentration and isotopic ratios are homogeneous throughout the volume of prepared gas. The nearly constant concentration during each pulse demonstrates homogeneous concentration, and the concentration from pulse to pulse is also nearly constant. The isotopic ratios during each pulse (not shown in FIG. 3) are also nearly constant, demonstrating that the water vapor isotopic ratio provided by the evaporator is homogeneous. This property enables the accurate determination of the isotopic ratios of the liquid water by analyzing a convenient time segment of each pulse. This advantageous property is in sharp contrast to conventional approaches, which typically require measuring the entire volume of prepared gas and analyzing all of the measurement time to obtain an accurate determination of the isotopic ratios of the original liquid water.

Figure 4:
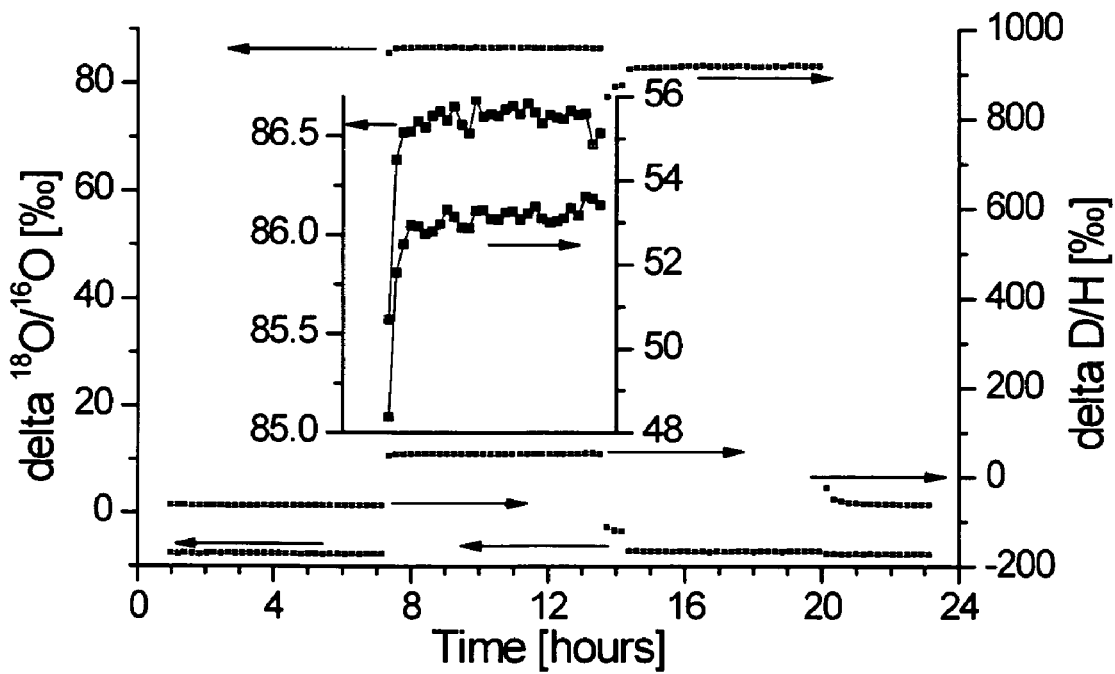
FIG. 4 shows measured liquid water isotope ratios as a function of time from an embodiment of the invention.

FIG. 4 shows the delta values of the liquid water samples as determined by the averaging of the delta values in time during the concentration pulses (of which FIG. 3 shows a subset). A delta value is the isotopic ratio normalized and referenced to the ratio of a standard (e.g. VSMOW). Delta values are stated in parts per thousand, denoted by ‰. In FIG. 4, each pair of delta values (one for $^{18}O/^{16}O$ and one for D/H) corresponds to one liquid sample injection. The arrows indicate which values are the oxygen ratio (left axis) and which are the deuterium ratio (right axis).

Figure 5:
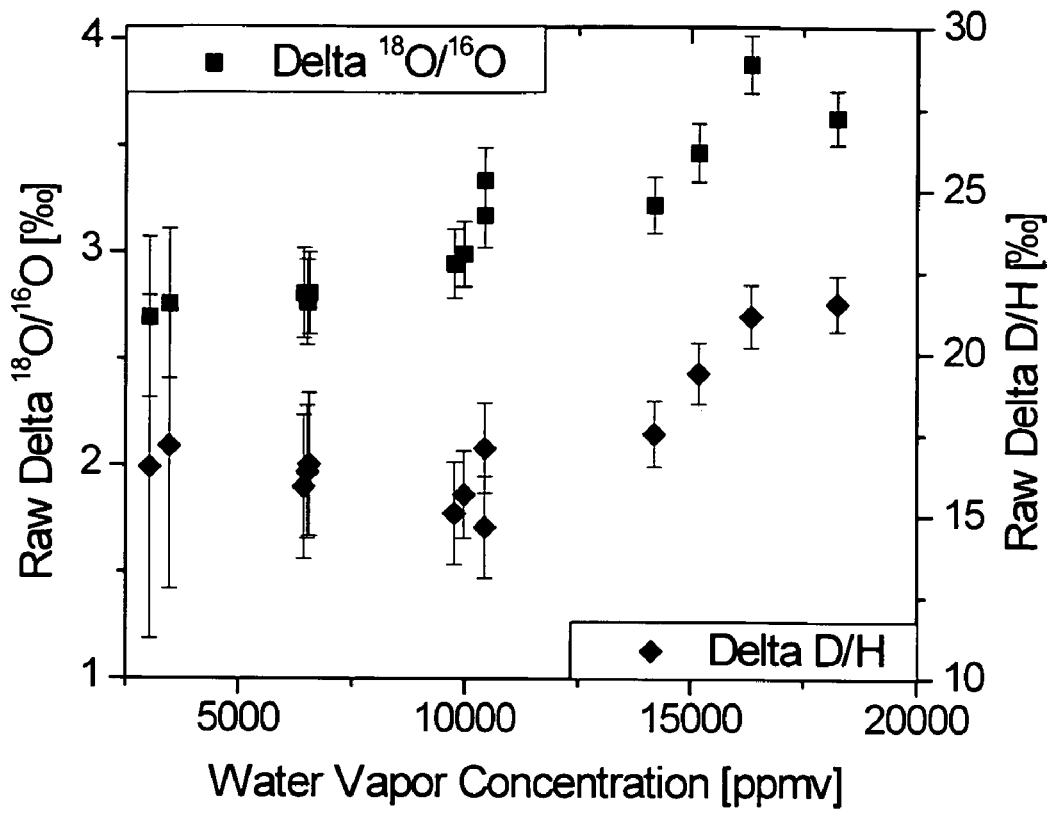
FIG. 5 shows isotopic ratios of a water reference measured at different water vapor concentrations from an embodiment of the invention.

FIG. 5 shows the dependence of raw delta value measurements on the concentration of water vapor. The same water (e.g. the same delta values) was used for all these measurements. The squares designate oxygen isotopologue delta value ($^{18}O/^{16}O$) measurements, and the diamonds designate deuterium/hydrogen delta value (D/H) measurements. The error bars denote uncertainties in the raw measurements. Such data can be inverted and used to adjust the raw delta value measurements to determine accurately the delta value of the liquid sample. As seen in FIG. 5, the dependence of the raw delta value measurement on water vapor concentration is weak, and so the adjustment is small and can be neglected for small variations in concentration.

The example in FIG. 4 includes large steps in the delta ratios, showing the effect of memory of previous liquid samples. The inset of FIG. 4 shows a magnification of the delta values following one of the steps. The delta values reach a new steady-state after typically 2-3 evaporator cycles. This is comparable to or superior to (i.e., less than) the number of cycles typically required of the current standard technology, isotope ratio mass spectrometry (IRMS) to reach a new steady state after such a step. The number of cycles to reach a new steady state tends to increase with increasing delta value step size.

Figure 6:
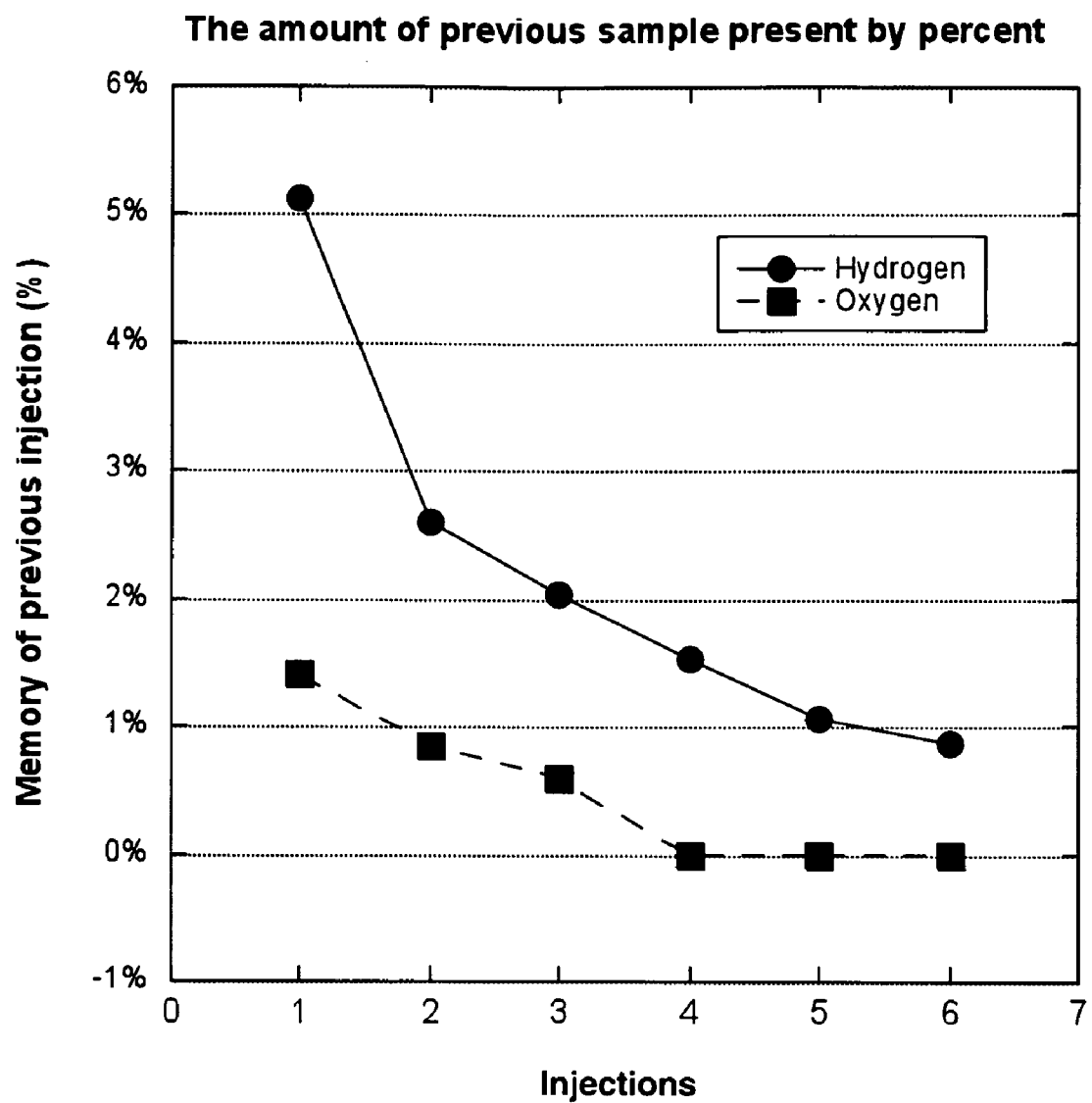
FIG. 6 shows an example of system memory effect of liquid water samples.

When running multiple liquid water samples, a very small amount of water lingers inside the evaporator from one sample to the next, because absolute evacuation and 100% removal of all previous water is usually impossible for reasonable measurement time scales. FIG. 6 shows measured memory for both hydrogen and oxygen. These results were obtained by establishing a baseline with a long series of identical first water samples having known first isotopic delta values, followed by making measurements of a series of identical second water samples having known second isotopic delta values. From this kind of measurement, the percentage effect of the baseline sample remaining in the first few measurements of the second water samples can be determined, and is shown on FIG. 6. In the experimental tests summarized in FIG. 6, oxygen memory is considerably smaller than hydrogen memory, and becomes essentially non-existent after 3 injections of identical sample. Likewise, the hydrogen memory is reduced to less than 2% after 3 injections. Over the course of an analysis run, the memory for each injection following a change of liquid water sample is typically very consistent, with standard deviations of 0.004 ‰, and 0.008 ‰ for hydrogen and oxygen respectively, in one experiment.

Once characterized, these memory effects can be alleviated by post-processing of the analysis data and applying a memory correction. In a simple theoretical model, the measured isotopic value of water injected into a system with memory is described by, $$M=X*T+(1-X)P, \quad (1)$$

where M is the measured value of a current injection, T is the true value for the current injection, X is a memory coefficient, and P is the measured value of the injection immediately prior to M.

The memory coefficient X can be determined by creating a situation where M, P, and T are known and where P and T differ. For example, in a situation where two different references (ref1 and ref2) are available, characterization as described above can give the true values T1 and T2 for the references. Once this information is available, the sample input can be switched to ref2 after a long series of ref1 inputs. In this situation, P in Eq. 1 is equal to T1, and T in Eq. 1 is equal to T2, so Eq. 1 can be solved for X to give $$X=(M-T1)/(T2-T1). \quad (2)$$

For example, the results of FIG. 6 would give X=0.95 for Hydrogen memory. Once the memory coefficient X has been determined, Eq. 1 can be solved for T in terms of X and measured quantities to give:

$$T=(M-(1-X)P)/X. \quad (3)$$

The result of Eq. 3 can be used to provide results for T given measured values for M and P, and the memory calibration factor X.

The method based on Eqs. 1-3 above can be regarded as based on a predetermined model of system memory effects that is a two-term linear combination of a current measurement and a measurement immediately prior to the current measurement. More complicated models involving a sum over two or more previous sample injections can describe the memory effect more accurately. In such cases, the predetermined model can be a linear combination of a current measurement and one or more measurements prior to the current measurement.

Figure 7:
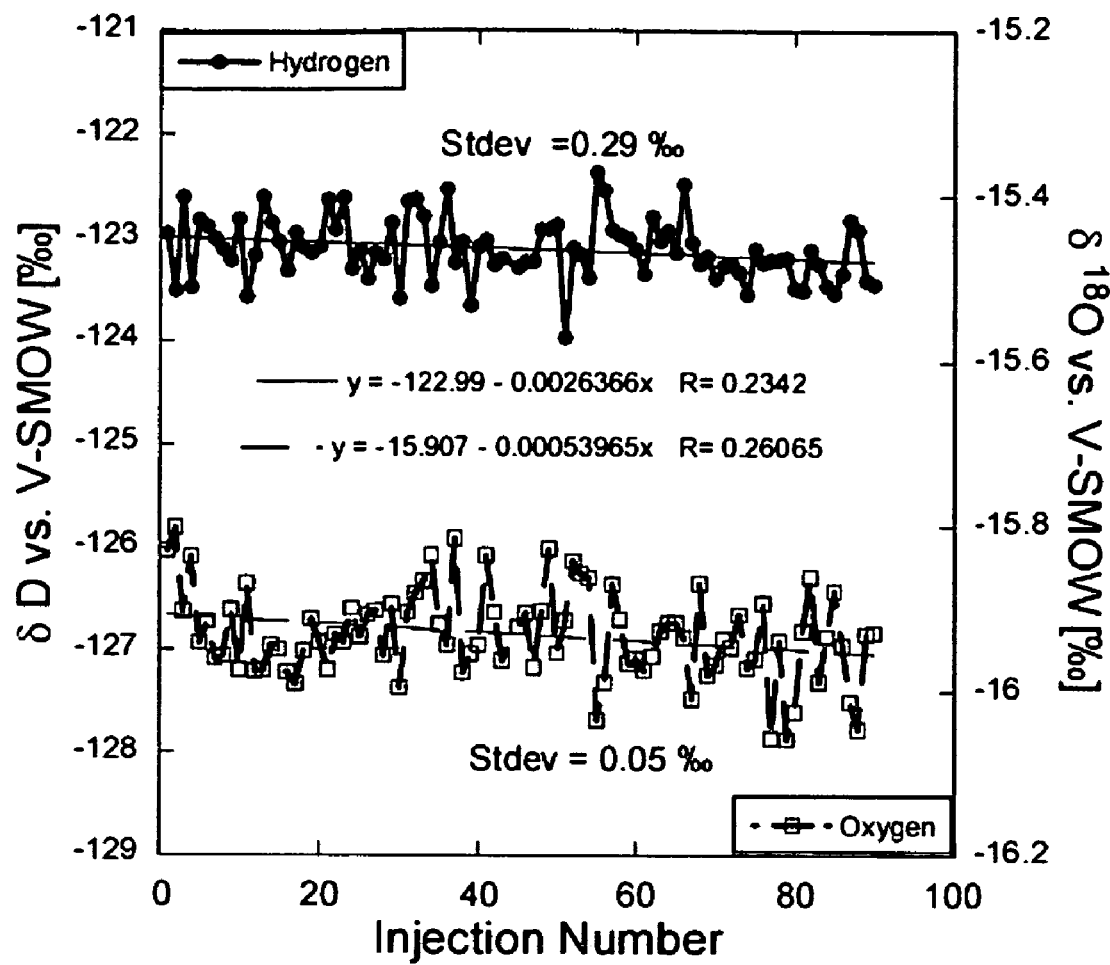
FIG. 7 shows drift measurements of liquid water samples from an embodiment of the invention.

The evaporator can be very stable, due to, among other things, strict temperature regulation of parts having gas-exposed surfaces. However, since the evaporator can theoretically be exposed to contaminants in the injected sample waters, it may be possible for the memory characteristics to change over long periods of time. This, along with any other possible sources of drift, can be addressed with the inclusion of one or more known standards within each run of multiple unknowns. This ensures correct calibration of the instrument, and results can be scaled to the absolute performance of known waters with certainty. Observations of instrument drift have been made by making over 180 injections of two different waters over a 24 hour period. The total drift of the isotopic determinations over this period were very small, less than 1.6 ‰ and 0.2 ‰ for hydrogen and oxygen respectively. FIG. 7 is a plot of the data used to determine the drift, along with slopes and standard deviations of the sample population.

Water samples with contaminants (mostly salts) in excess of 19,000 micro siemens have been analyzed without noticeable affect on the isotopic determinations. When analyzing contaminated water samples, care must be taken to clean the syringe and guard against clogging, especially if the contamination includes solid particles suspended in the liquid.

Figure 8A:
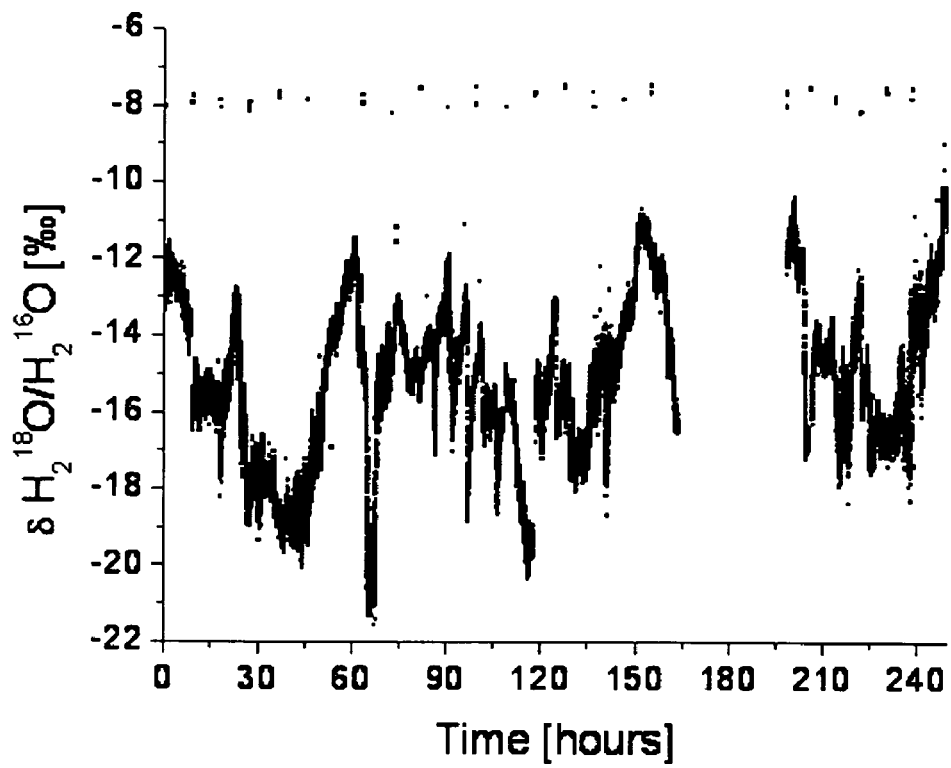
FIGS. 8*a-b* show calibrated water vapor isotopic ratio measurements from an embodiment of the invention.
Figure 8B:
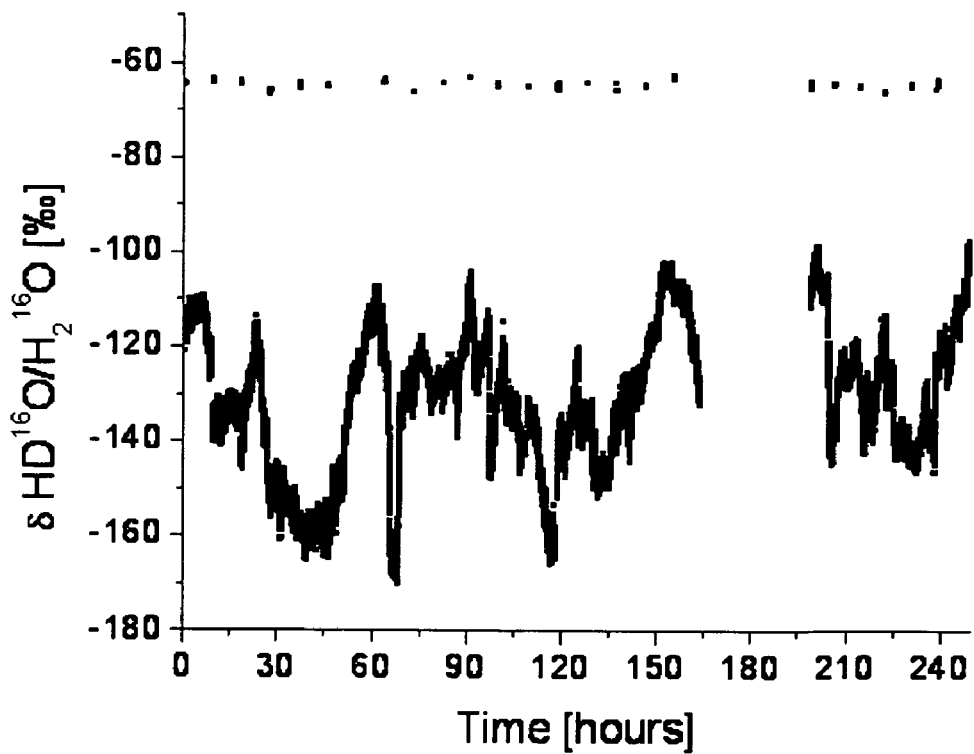

FIGS. 8a-b shows an example of water vapor concentration measurements in time according to an embodiment of the invention, where the evaporator executes a few cycles and then pauses for several hours before repeating another few cycles. In this example, the alternate gas source was ambient air admitted to the system in alternate input line 112 of FIG. 1. The isotopic measurements between evaporator cycles are of the ambient air, and the liquid injected during the evaporator cycles is of known isotopic content, and can be used to verify or adjust the calibration of the system. FIG. 8a shows the oxygen delta values and FIG. 8b shows the deuterium delta values. The delta values around −8 in FIG. 8a and around −55 in FIG. 8b are of the liquid samples. The capability to alternate isotopic measurements of water between vapor in a sample gas (e.g. ambient air) and reference vapor accurately derived from liquid calibration standards is a significant advantage provided by embodiments of the invention.

In preferred embodiments of the invention, the liquid sample is a calibration reference, and the conditioned vapor sample provided by the evaporator is an accurate gas-phase calibration reference derived from the liquid calibration reference. Such a gas-phase calibration reference can be employed to provide calibration for a gaseous sample or for a second liquid sample (e.g., by performing alternating measurements as described above). Such second liquid samples can also be evaporated and conditioned as described above (e.g., by alternating water injections into a single evaporator, or by adding a second evaporator to the right of three-way valve 106 on FIG. 1).

The invention claimed is:

1. A method of preparing a liquid sample for analysis, the method comprising:
   admitting a first liquid sample to a sample chamber;
   completely evaporating said first liquid sample in said sample chamber to provide sample vapor;
   admitting a carrier gas to said sample chamber;
   allowing said sample vapor and said carrier gas to statically equilibrate for a predetermined time to provide a conditioned sample in said sample chamber;
   providing said conditioned sample as an output for analysis.

2. The method of claim 1, wherein said predetermined time is selected such that said conditioned sample has substantially uniform sample vapor concentration within said sample chamber.

3. The method of claim 1, wherein said predetermined time is selected such that said conditioned sample has substantially uniform sample vapor isotopic ratio within said sample chamber.

4. The method of claim 1, wherein said first liquid sample is a calibration standard, and further comprising using said conditioned sample as a calibration reference for said analysis.

5. The method of claim 4, further comprising performing alternating measurements of said calibration reference and a gaseous sample, whereby measurements of said gaseous sample calibrated with respect to said first liquid sample are provided.

6. The method of claim 4, further comprising performing alternating measurements of said calibration reference and a second liquid sample, whereby measurements of said second liquid sample calibrated with respect to said first liquid sample are provided.

7. The method of claim 1, wherein said analysis comprises isotopic ratio analysis.

8. The method of claim 1, wherein said analysis includes determination of sample vapor concentration.

9. The method of claim 1, wherein said analysis includes determination of one or more analyte concentrations in said first liquid sample.

10. The method of claim 1, wherein said first liquid sample comprises water.

11. The method of claim 1, further comprising performing one or more dry flush steps prior to said admitting a first liquid sample to said sample chamber, wherein each of said dry flush steps comprises:
    admitting a dry carrier gas substantially free of vapor of said first liquid sample to said sample chamber, followed by
    removing said dry carrier gas from said sample chamber.

12. The method of claim 1, further comprising performing one or more wet flush steps prior to said admitting a first liquid sample to said sample chamber, wherein each of said wet flush steps comprises:
    admitting a wet carrier gas including vapor of said first liquid sample to said sample chamber, followed by
    removing said wet carrier gas from said sample chamber.

13. The method of claim 1, further comprising substantially evacuating said sample chamber prior to said admitting said first liquid sample.

14. The method of claim 13, wherein said substantially evacuating said sample chamber is performed prior to admitting said carrier gas.

15. The method of claim 1, further comprising maintaining said chamber at an elevated temperature.

16. The method of claim 1, wherein all of said carrier gas is admitted to said sample chamber before said first liquid sample is admitted to said sample chamber.

17. The method of claim 1, wherein all of said carrier gas is admitted to said sample chamber after said first liquid sample is admitted to said sample chamber.

18. The method of claim 1, wherein some of said carrier gas is admitted to said sample chamber before said first liquid sample is admitted to said sample chamber, and wherein some of said carrier gas is admitted to said sample chamber after said first liquid sample is admitted to said sample chamber.

19. The method of claim 1, further comprising determining a calibration of system memory.

20. The method of claim 19, further comprising providing corrected analysis output results based on said calibration of system memory and a predetermined model of system memory effects.

21. The method of claim 20, wherein said predetermined model is a two-term linear combination of a current measurement and a measurement immediately prior to said current measurement.

22. The method of claim 20, wherein said predetermined model is a linear combination of a current measurement and one or more measurements prior to said current measurement.

23. The method of claim 1, wherein said first liquid sample is. admitted to said sample chamber using a septum and syringe.

24. The method of claim 1, wherein said first liquid sample is admitted to said sample chamber using a syringe pump or metering pump.

25. The method of claim 1, wherein a volume of said first liquid sample is between 0.1 microliters and 10 microliters.

26. A method of preparing a liquid sample for analysis, the method comprising:
    repeating the method of claim 1 two or more times, each repetition having a corresponding sample volume of said first liquid sample;
    wherein an average sample volume is defined to be an average of said sample volumes;
    wherein said sample volumes differ from said average sample volume by less than 10% of said average sample volume.

* * * * *